(12) United States Patent
Dresser et al.

(10) Patent No.: US 10,617,468 B1
(45) Date of Patent: Apr. 14, 2020

(54) SYSTEM AND METHOD FOR TISSUE TREATMENT

(71) Applicant: Avava, Inc., Boston, MA (US)

(72) Inventors: Charles Holland Dresser, Wayland, MA (US); Jayant Bhawalkar, Auburndale, MA (US); Joseph Ting, Acton, MA (US)

(73) Assignee: Avava, Inc., Waltham, MA (US)

( * ) Notice: Subject to any disclaimer, the term of this patent is extended or adjusted under 35 U.S.C. 154(b) by 0 days.

(21) Appl. No.: 16/237,367

(22) Filed: Dec. 31, 2018

(51) Int. Cl.
*A61B 18/20* (2006.01)
*A61B 18/22* (2006.01)
*A61B 18/00* (2006.01)

(52) U.S. Cl.
CPC .......... *A61B 18/201* (2013.01); *A61B 18/203* (2013.01); *A61B 2018/00005* (2013.01); *A61B 2018/0047* (2013.01); *A61B 2018/2015* (2013.01); *A61B 2018/2253* (2017.05)

(58) Field of Classification Search
CPC combination set(s) only.
See application file for complete search history.

(56) References Cited

U.S. PATENT DOCUMENTS

| | | | |
|---|---|---|---|
| 6,096,029 A * | 8/2000 | O'Donnell, Jr. | A61B 18/203 606/3 |
| 6,264,649 B1 | 7/2001 | Whitcroft et al. | |
| 6,436,094 B1 | 8/2002 | Reuter | |
| 6,817,997 B2 | 11/2004 | Furuno et al. | |
| 8,696,655 B2 | 4/2014 | Dolleris et al. | |
| 8,728,064 B2 | 5/2014 | Schomacker et al. | |
| 9,067,062 B2 | 6/2015 | Hilly | |
| 9,554,856 B2 | 1/2017 | McMillan et al. | |

(Continued)

FOREIGN PATENT DOCUMENTS

| JP | 2015146329 A | 8/2015 |
|---|---|---|
| WO | 2018/112261 A1 | 6/2018 |

OTHER PUBLICATIONS

<https://inis.iaea.org/search/search.aspx?orig_q=RN:47081278>, Analysis of Laser Modes in High Power Unstable Resonators with Intra-Cavity Wavefront Aberrations, Journal of Optics (Online); ISSN 2040-8986, v. 17(4); [11p.], United Kingdom, 2015.

(Continued)

*Primary Examiner* — Scott Luan
(74) *Attorney, Agent, or Firm* — Mintz Levin Cohn Ferris Glovsky and Popeo, P.C.

(57) ABSTRACT

A cooling element includes a frame including one or more datums. The cooling element also includes a first window including a first proximal surface and a first distal surface. The first window is sealed to the frame. The cooling element further includes a second window sealed to the frame. The second window includes a second proximal surface and a second distal surface. The second window is configured to contact a target tissue or a tissue adjacent to the target tissue via the second distal surface. The cooing element also includes a coolant chamber located between the first distal surface of the first window and the second proximal surface of the second window and configured to receive a coolant. The first window, the second window and the coolant chamber are configured to receive and electromagnetic radiation (EMR), and transmit a portion of the received EMR to the target tissue.

29 Claims, 12 Drawing Sheets

(56) References Cited

U.S. PATENT DOCUMENTS

| | | |
|---|---|---|
| 2001/0007068 A1 | 7/2001 | Ota et al. |
| 2008/0125771 A1 | 5/2008 | Lau et al. |
| 2008/0132886 A1* | 6/2008 | Cohen .................. A61B 18/203 606/34 |
| 2012/0179227 A1* | 7/2012 | Schomacker ........ A61B 18/203 607/89 |
| 2013/0066237 A1 | 3/2013 | Smotrich et al. |
| 2013/0150841 A1 | 6/2013 | Schomacker et al. |
| 2016/0089202 A1 | 3/2016 | Schomacker et al. |
| 2016/0199132 A1 | 7/2016 | Anderson et al. |
| 2018/0177550 A1* | 6/2018 | Anderson ............ A61B 18/203 |

OTHER PUBLICATIONS

Notification of Transmittal of the International Search Report and the Written Opinion of the International Searching Authority issued in corresponding International Application No. PCT/US18/68192, dated Apr. 11, 2019, 11 pages.

* cited by examiner

SYSTEM AND METHOD FOR TISSUE TREATMENT

BACKGROUND

Various conditions can be treated with the application of light or optical energy of certain wavelengths. Many challenges exist in delivering the energy to the appropriate target structure (e.g., tissue such as the skin) without damaging tissue structures adjacent to the target structure. These challenges include delivery of energy at an appropriate wavelength with sufficient fluence, as well as the ability to effectively and efficiently scan the target structure with the light or optical energy.

Melasma is an example of one skin disorder of unknown etiology that causes a blotchy hyperpigmentation, often in the facial area. This condition is more common in women than in men. Although the specific cause(s) of melasma may not be well-understood, the pigmented appearance of melasma can be aggravated by certain conditions such as pregnancy, sun exposure, certain medications, such as, e.g., oral contraceptives, hormonal levels, genetics, etc. Exemplary symptoms of melasma include dark, irregularly-shaped patches or macules, which are commonly found on the upper cheek, nose, upper lip, and forehead. These patches often develop gradually over time. Melasma does not appear to cause any other symptoms, nor have other detrimental effects, beyond the cosmetic discoloration.

Unlike many pigmented structures that are typically present in the epidermal region of skin (i.e., at or near the tissue surface), dermal (or deep) melasma is often characterized by widespread presence of melanin and melanophages (including, e.g., excessively-pigmented cells) in portions or regions of the underlying dermis. Accordingly, treatment of dermal melasma (e.g., lightening of the appearance of darkened pigmented regions) can be particularly challenging because of the presence of the greater difficulty in accessing and affecting such pigmented cells and structures located deeper within the skin. Accordingly, conventional skin rejuvenation treatments such as facial peels (laser or chemical), dermabrasion, topical agents, and the like, which primarily affect the overlying epidermis, may not be effective in treating dermal melasma.

SUMMARY

It has been observed that application of light or optical energy of certain wavelengths can be strongly absorbed by pigmented cells, thereby damaging them. However, an effective treatment of dermal melasma using optical energy introduces several obstacles. For example, pigmented cells in the dermis must be targeted with sufficient optical energy of appropriate wavelength(s) to disrupt or damage them, which may release or destroy some of the pigmentation and reduce the pigmented appearance. However, such energy can be absorbed by pigment (e.g., chromophores) in the overlying skin tissue, such as the epidermis and upper dermis. This near-surface absorption can lead to excessive damage of the outer portion of the skin, and insufficient delivery of energy to the deeper dermis to affect the pigmented cells therein. Moreover, thermal injury to melanocytes located in the basal layer of the epidermis can trigger an increase in the production of melanin and, thermal damage resulting in destruction of the melanocytes can cause hypopigmentation. Therefore, it is desirable to cool (i.e., transfer heat away from) tissue that is not being targeted and especially pigmented epidermal tissue located just above a dermal melasma macule. The cooling ideally will occur simultaneously with the treatment radiation and over the same tissue surface as the radiation.

Fractional approaches have been developed that involve application of optical energy to small, discrete treatment locations on the skin that are separated by healthy tissue to facilitate healing. Accurately targeting the treatment locations (e.g., located in dermal layer) with desirable specificity while avoiding damage to healthy tissue around the treatment location (e.g., in the epidermal layer) can be challenging. This requires, for example, an optical system with high numerical aperture (NA) for focusing a laser beam to a treatment location. Additionally, the optical system should be able to scan the focused beam over large affected regions (e.g., several square centimeters). Therefore, it is desirable to develop an optical system that can have high numerical aperture, and is capable of scanning over large affected regions. It is also desirable that an interface establish a robust contact with the treatment region and stabilize the treatment region, so that a depth of the focused laser beam may be maintained within the treatment region. Furthermore, it can be advantageous that the interface cool the treatment region coincidently with the treatment radiation to prevent undesired thermal injury. For at least the reasons outlined above, improved methods, systems, and devices for EMR-based (e.g., laser-based) tissue treatment are provided.

In one implementation, a system includes an optical element configured to receive an electromagnetic radiation (EMR), and focus the EMR along an optical axis to a focal region in a target tissue. The system also includes a cooling element down-beam from the optical element and configured to receive the focusing EMR. The cooling element includes a first window comprising a first proximal surface and a first distal surface. The first window is sealed to the frame. The cooling element further includes a second window sealed to the frame. The second window includes a second proximal surface and a second distal surface. The second window is configured to contact a target tissue or a tissue adjacent to the target tissue via the second distal surface. The cooing element also includes a coolant chamber located between the first distal surface of the first window and the second proximal surface of the second window and configured to receive a coolant. The first window, the second window and the coolant chamber are configured to receive and electromagnetic radiation (EMR), and transmit a portion of the received EMR to the target tissue.

In one implementation, the controller is configured to vary a first distance between the focal region and the second distal surface of the second window along the optical axis by varying a second distance between the optical element and the second distal surface of the second window along the optical axis. In another implementation, the first distance varies between a first predetermined value and a second predetermined value as the focal region traverses along the treatment path in the target tissue. In yet another implementation, a difference between the first predetermined value and the second predetermined value is less than 0.25 mm. In another implementation, the first predetermined value is 0.001 mm and the second predetermined value is 10 mm.

In one implementation, the controller is configured to vary a first distance between the focal region and the second distal surface of the second window along the optical axis by varying a divergence associated with the EMR. In another implementation, the system further includes a scanner. The scanner is configured to receive a control signal from the controller and move the optical element along the first scan path based on the control signal. In yet another implementation, the first scan path is substantially parallel to the second distal surface of the second window.

In one implementation, the controller is configured to vary an intensity of the EMR radiation. In another implementation, the controller is configured to vary a flow rate of the coolant in the coolant chamber. In yet another implementation, the optical element has a numerical aperture (NA) in the range of about 0.1 to about 1.0.

In one implementation, the EMR has an average power in the range of about 1 W to about 100 W. In another implementation, the EMR includes a pulsed laser beam having a wavelength in a range of about 400 nm to about 4000 nm. In yet another implementation, the EMR is configured to generate thermionic plasma in the focal region. In another implementation, the cooling element further includes a gas source configured to direct a gas at the first window, the gas configured to prevent condensation on the first window.

In one implementation, a method includes generating a focusing electromagnetic radiation (EMR), and transmitting the focusing EMR through a cooling element. The cooling element includes a first window comprising a first proximal surface and a first distal surface. The first window is sealed to the frame. The cooling element further includes a second window sealed to the frame. The second window includes a second proximal surface and a second distal surface. The second window is configured to contact a target tissue or a tissue adjacent to the target tissue via the second distal surface. The cooing element also includes a coolant chamber located between the first distal surface of the first window and the second proximal surface of the second window and configured to receive a coolant. The method further includes directing the focusing EMR to a focal region in the target tissue.

In one implementation, generating the focusing EMR includes placing an optical lens along an optical axis of the EMR. In another implementation, the method further includes varying a depth of the focal region in the target tissue by varying a location of the optical lens along the optical axis. In yet another implementation, the depth of the focal region ranges from about 0.001 mm to about 10 mm.

In one implementation, the method further includes scanning the focusing EMR along a treatment path in the target tissue. In another implementation, the focusing EMR beam is scanned along a treatment path by moving the optical element substantially parallel to the second distal end of the second window.

BRIEF DESCRIPTION OF THE DRAWINGS

Embodiments of the disclosure will be more fully understood from the following detailed description taken in conjunction with the accompanying drawings, in which.

Figure 1:
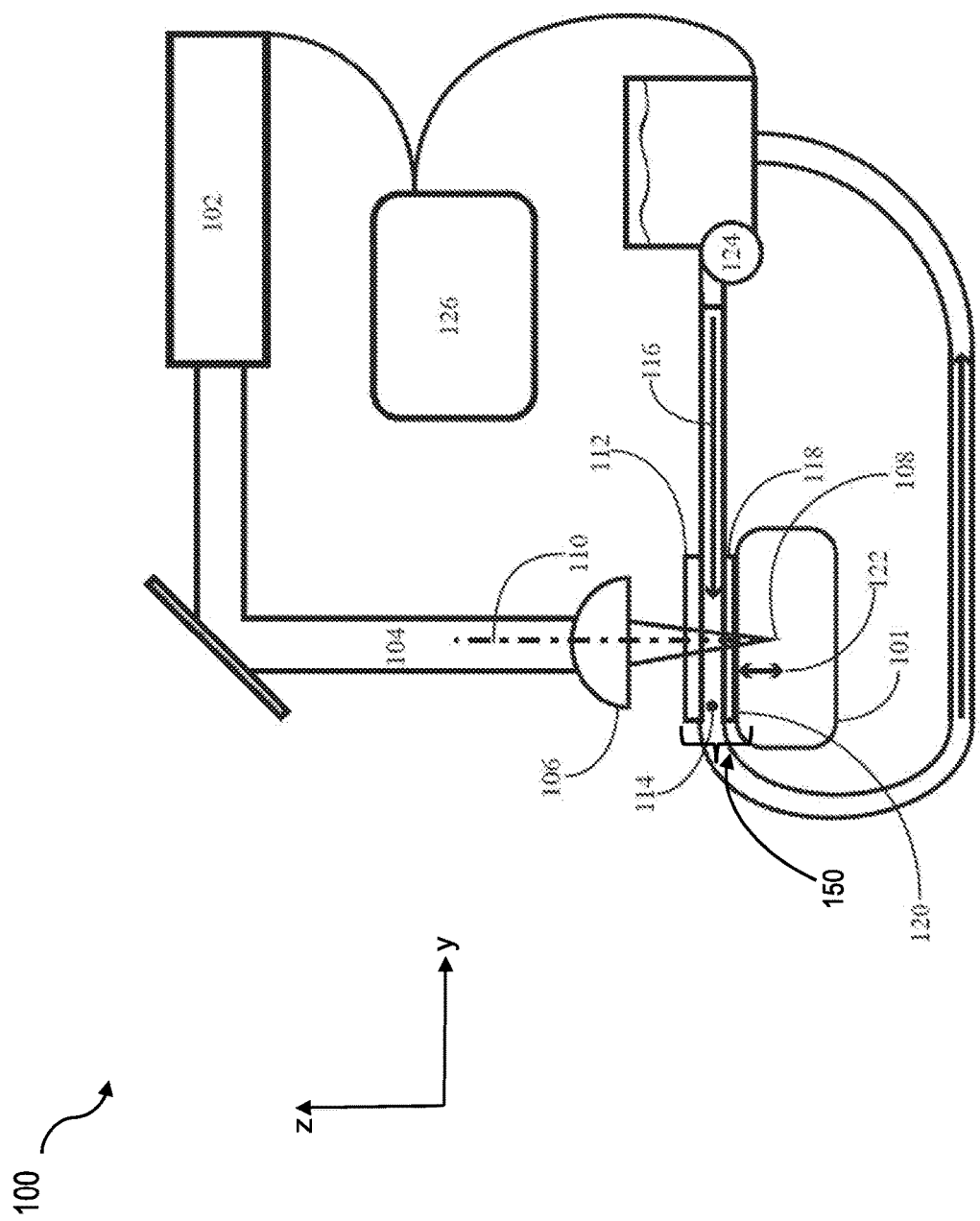
FIG. 1 schematically represents a system to irradiate and cool a tissue, according to some embodiments.

It is noted that the drawings are not necessarily to scale. The drawings are intended to depict only typical aspects of the subject matter disclosed herein, and therefore should not be considered as limiting the scope of the disclosure. Those skilled in the art will understand that the systems, devices, and methods specifically described herein and illustrated in the accompanying drawings are non-limiting exemplary embodiments and that the scope of the present embodiments are defined solely by the claims.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. The features illustrated or described in connection with one exemplary embodiment may be combined with the features of other embodiments. Such modifications and variations are intended to be included within the scope of the present invention.

Some embodiments of the disclosure are discussed in detail below with respect to treatment of pigmentary conditions of the skin, such as melasma, to improve the appearance of such a pigmentary condition. However, the disclosed embodiments can be employed for treatment of other pigmentary and non-pigmentary conditions and other tissue and non-tissue targets without limit. Examples of pigmentary conditions can include, but are not limited to, post inflammatory hyperpigmentation, dark skin surrounding eyes, dark eyes, café au lait patches, Becker's nevi, Nevus of Ota, congenital melanocytic nevi, freckles/lentigo, hemosiderin rich structures, pigmented gallstones, lutein, zeaxanthin, rhodopsin, carotenoid, biliverdin, bilirubin and hemoglobin rich structures, and tattoo-containing tissue. Examples of non-pigmentary conditions can include, but are not limited to, hair follicles, hair shaft, vascular lesions, infectious conditions, sebaceous glands, acne, and the like. Examples of non-skin tissues can include, but are not limited to, soft tissues, such as cartilage, mucosa and serosa, and hard tissues, such as bone and dental enamel.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, some high numerical aperture (NA) optical treatment systems are described that can focus electromagnetic radiation (EMR) (e.g., a laser beam) to a treatment region in a tissue. The focused laser beam can deliver optical energy to the treatment region without harming the surrounding tissue. The delivered optical energy can, for example, disrupt pigmented chromophores and/or targets in a treatment region of the dermal layer of the skin, without affecting the surrounding regions (e.g., overlying epidermal layer, other portions of the dermal layer, and the like) or within other pigmented target areas of the skin or tissue surrounded by unaffected and non-targeted areas. In other implementations, the delivered optical energy can cause tattoo removal or alteration, or hemoglobin-related treatment. During a typical treatment a large amount of radiation (e.g., greater than 1 W, 5 W, 10 W, 20 W, or 30 W average power depending on wavelength) can be delivered to the tissue. These radiation levels ultimately can result in bulk heating of the tissue and potentially cause thermal damage. In order to prevent bulk heating of the tissue, cooling of the tissue must be performed. In order for the cooling to be most effective, cooling is performed at the same place and at the same time as the irradiation. Previous methods of cooling have performed cooling at the same place, but not at the same time (e.g., cryogenic cooling). Still other methods for cooling have been performed, which cool at the same time, but not over the selfsame area as the irradiation.

Exemplary methods and devices for treating skin conditions with light or optical energy are disclosed in U.S. Patent Application Publication No. 2016/0199132, entitled "Method and Apparatus for Treating Dermal Melasma," and U.S. Provisional Application No. 62/438,818, entitled "Method and Apparatus for Selective Treatment of Dermal Melasma," each of which is hereby incorporated by reference herein in their entirety.

FIG. 1 illustrates an exemplary embodiment of a treatment system 100 that can irradiate and cool a tissue 101. An electromagnetic radiation (EMR) source 102, such as a laser, generates an EMR beam 104. According to some embodiments, the EMR beam 104 has a wavelength in a range of between 100 nanometer (nm) and 15000 nm (e.g., between 400 nm and 4000 nm). An exemplary EMR source 102 can be a Q-Smart 450 from Quantel of Les Ulis, France. The Q-Smart 450 can be capable of generating an EMR beam 104 (e.g., pulsed beam) having a wavelength of 1064 nm, a pulse duration of between 6 nanoseconds (nS) and 20 nS, a repetition rate up to 40 Hz, and a pulse energy up to 450 mJ. Another exemplary EMR source 102 is the Coherent Diamond FLQ fiber laser from Coherent of Santa Clara, Calif. The EMR beam 104 generated by the Diamond FLQ fiber laser can have an average power up to 10 W, 20 W, 50 W, or 100 W, a pulse duration of about 100 nS, a pulse energy up to 1 mJ, and a pulse repetition rate between 20 KHz and 100 KHz. The EMR beam 104 can be focused by an optical element 106 causing the EMR beam 104 to converge to a focus 108 (or a "focal region") as it propagates along an optical axis 110. According to some embodiments, the EMR beam 104 converges to a focus 108 with a numerical aperture between 0.1 and 1.0 (e.g., 0.5).

The treatment system 100 can include a cooling element 150 comprising a first window 112, a chamber 114 configured to receive/contain a flow of coolant 116 (e.g., fluid coolant), and a second window 118. The cooling element can be located downs-beam from the optical element 106. The term "down-beam" indicates that the EMR beam 104 first impinges on the optical element 106 and then impinges on the cooling element 150. Said another way, the optical element 106 is located up-beam from the cooling element 150.

The EMR beam 104 can be transmitted through a cooling element 150 comprising a first window 112, a chamber 114 configured to receive/contain a flow of coolant 116, and a second window 118. For example, the first window 112, coolant 116 and the second window 118 can substantially transmit the EMR beam 104. According to some embodiments, the EMR beam can be converging (e.g., focused) as it is transmitted through the first window 112, the chamber 114, the flow of coolant 116, and the second window 118. The EMR beam 104 can come to a focus 108 after propagating through a distal surface 120 of the second window 118. There is a working distance 122 between the focus 108 and the distal surface 120 of the second window 118. According to some embodiments, the working distance 122 can have values ranging between 0.001 millimeter (mm) and 100 mm (e.g., 0.5 mm, 1.0 mm, and 10 mm).

According to some embodiments, a coolant flow source 124 can induce the flow of coolant 116, which can be contained/received by the chamber 114 located between the first window 112 and the second window 118 (e.g., between a distal surface of first window 112 and proximal surface of second window 118). An exemplary coolant flow source is a compact chiller (Part No. UC160-190) from Steady State Cooling Systems of Wappingers Falls, N.Y. The UC160-190 is capable of generating a coolant flow 124 having a flow rate of 500 ml/min±50 ml/min at 9 psig, a maximum pressure of 30 psig, and a coolant temperature between 2° C. and 45° C. A coolant can be generally transmissive (e.g., greater than 50% transmissivity) at the wavelength of the EMR beam 104. For example, a mixture of propylene-glycol and water is generally transmissive over a wavelength range that encompasses the visible spectrum and 1064 nm.

According to some embodiments, the treatment system 100 further comprises a controller 126. The controller can be configured to control the EMR source 102 and the coolant flow source 124, the direction of transmission of EMR beam 104, location/motion of the optical element 106 (e.g., path of the optical element 106 with respect to the cooling element 150), etc. According to some embodiments, temperature of the coolant 116 is controlled within a few degrees Celsius of a set point. Exemplary coolant temperature set points include temperatures less than −10° C., 0° C., 5° C., and temperatures greater than 10° C. According to some implementations, the controller 126 controls one or more parameters of the coolant flow source 124, including a coolant set point temperature and a coolant flow rate. According to some implementations, the controller 126 controls one or more parameters of the EMR source 102 including: a pulse duration, a repetition rate, an EMR interlock or gate signal, a pulse energy, an average power, etc.

According to some embodiments, the treatment system 100 is configured to generate a plasma in the tissue 101 at or near the location of the focus 108. The plasma, in some embodiments, can be generated through optical means, such as photoionization. In order to produce plasma via photoionization, a large energy density may be required (e.g., for an EMR pulse having pulse duration in nanosecond range). For example, an irradiance threshold for photoionization of water can be as high as $10^{13}$ W/cm$^2$ (e.g., between $10^5$ W/cm$^2$ to $10^{13}$ W/cm$^2$). In other embodiments, the plasma can be generated by thermionic emission of electrons. Thermionic generation of plasma can take place in the presence of a chromophore (e.g., a material configured to absorb EMR beam 104) located at or near the focus 108 of the EMR beam 104. A high energy density at focus can result in the ionization of the chromophore and selective thermal damage to the chromophore and in some cases to materials near the chromophore. For example, an irradiance threshold for thermionic ionization in an absorbing medium of an EMR pulse having pulse duration in the nanosecond range can as low as $10^9$ W/cm$^2$), Although the selective nature of the converging EMR beam 104 and focus 108 can prevent immediate heating of non-targeted tissue, bulk heating can still occur over many EMR pulses above or near one or more focus 108 locations.

According to some implementations, the cooling element 150 can cool the tissue 101 as it is being irradiated by the EMR beam 104. In some implementations, a thermal path can run from the focus 108 (e.g., parallel/collinear with the optical axis 110) and through the tissue 101, an outer surface of the tissue 101, the distal surface 120 of the second window 118, the second window 118, and finally to the flow of coolant 116. This thermal path can be the shortest path from the focus 108 out of the tissue 101 and to the distal surface 120 of the second window 118 (e.g., the shortest path through the tissue 101). For this reason, bulk heat of the tissue 101 can be efficiently transferred (e.g., from the location of the focus 108) to the coolant 116. Because the coolant and the windows are both transmissive at the wavelength of the EMR beam, cooling may be performed simultaneously along with irradiation. Some treatments can require that the location of the focus 108 within the tissue be carefully controlled and at times varied. In these cases, it can be desirable for the location of the distal surface 120 of the second window 118 relative the focus 108 to be known and/or controlled. For example, sensors (e.g., accelerometers, position detectors, etc.) can detect the location and/or motion of the second window 118 (or cooling element 150) and can convey this information to the controller 126. This can allow to track the location and/or motion of the second window 118 (or cooling element 150).

Figure 2A:
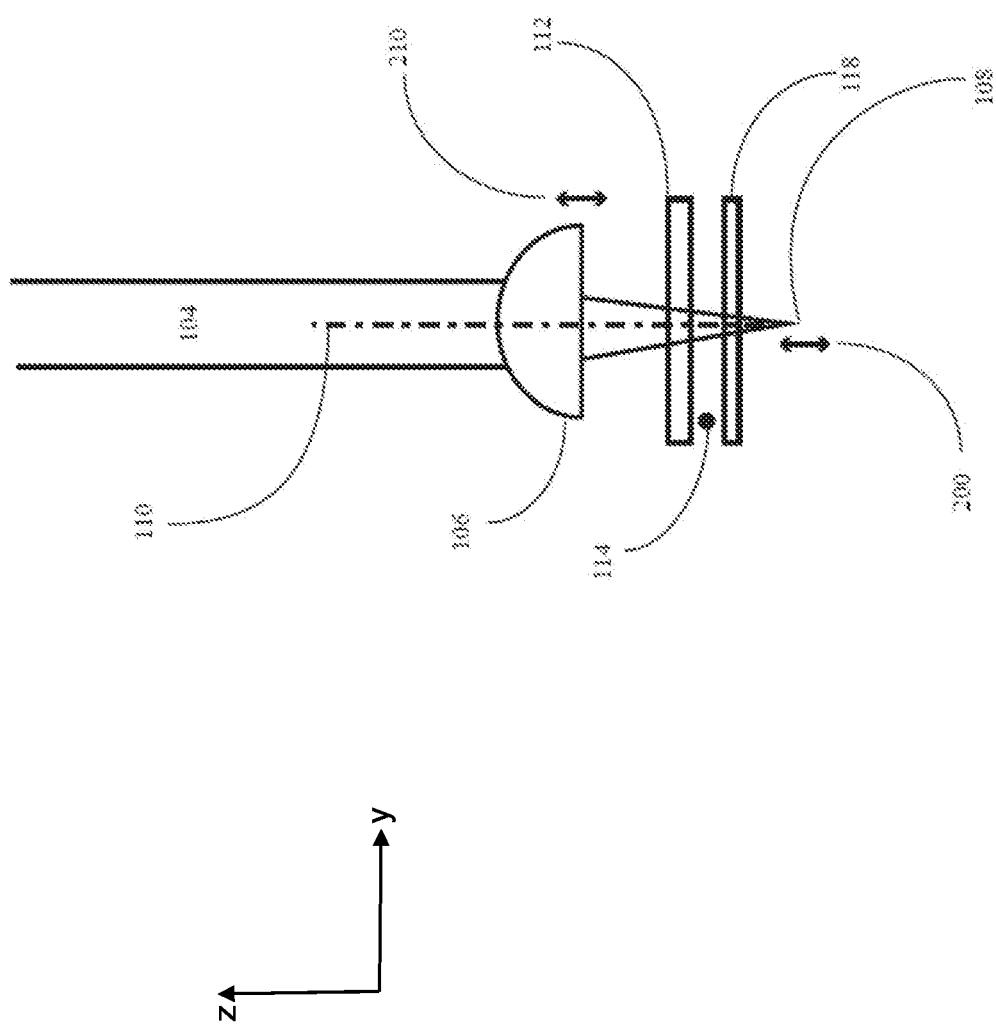
FIG. 2A schematically represents a system for varying a working distance of a focus of an electromagnetic radiation beam, according to some embodiments.
Figure 2B:
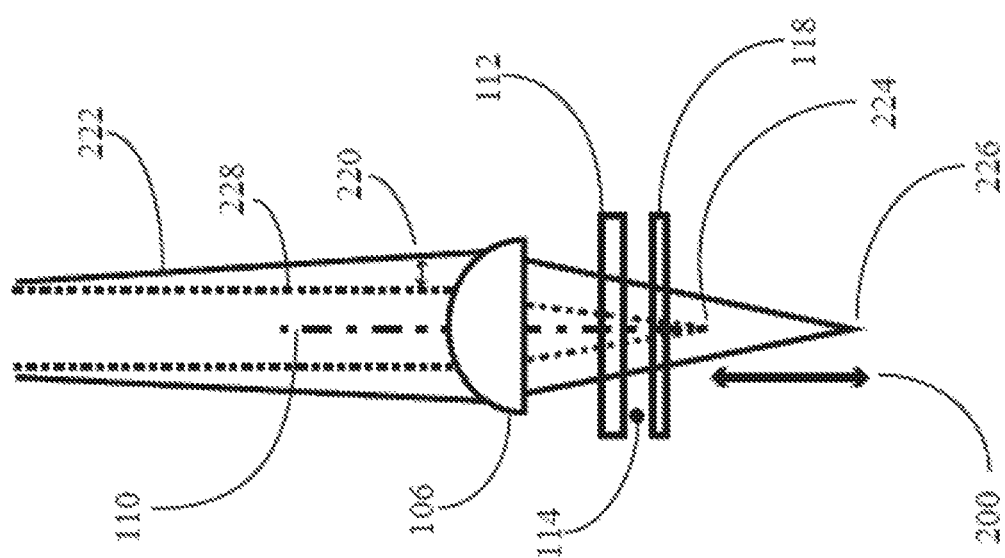
FIG. 2B schematically represents another system for varying a working distance of a focus of an electromagnetic radiation beam, according to some embodiments.

Dermal melasma may be treated through selective thermionic plasma in pigment containing dermis. In order to perform this treatment, it can be desirable to have the focus 108 of an EMR beam 104 at or near (e.g., 2× a Rayleigh range) the depth of the pigment within the dermis (e.g., 100 µm to 1 mm beneath the surface of the tissue 101). Referring now to FIGS. 2A-2B, a variation 200 of depth of the focus 108 location is shown. FIG. 2A schematically shows variation 200 of depth of the focus 108 according to some embodiments. Translating 210 the optical element 106 relative to the second window 118 along the optical axis 110 (e.g., z-axis) produces a corresponding variation 200 of depth of the focus 108. According to some embodiments, optic translation 210 can be generated by a stage and controlled by the controller. An exemplary stage is a M3-FS Focus Module from NewScale Technologies of Victor N.Y. In some versions, the controller 126 controls one or more parameters of the stage, including: acceleration, velocity, and position.

According to some embodiments, depth of the focus 108 can be varied (e.g., by variation 200) by a corresponding change in divergence 220 of a diverging EMR beam 222. Referring to FIG. 2B, depth can be varied 200 from a first focus location 224 to a second focus location 226. The first focus location 224 is produced by a wave front change introduced by the optical element 106 on a first EMR beam 228 having negligible divergence. The second focus location 226 is produced by the same optical element 106, but is located a different from the first focus location 224, because of the added divergence 220. According to some implementations, the change in divergence 220 is provided from an adaptive optic, such as a focus variable lens. An exemplary focus variable lens is an Optotune Part No. EL-10-42-OF from Optotune Switzerland AG. Because of the extreme lateral (e.g., x-axis and y-axis) selectivity (e.g., narrowness) of the focus 108, it can be desirable to scan the focus 108 over multiple locations in the tissue 101. In some implementations, the controller 126 can control one or more parameters of the adaptive optic (e.g. to vary the divergence of the EMR beam).

Figure 3:
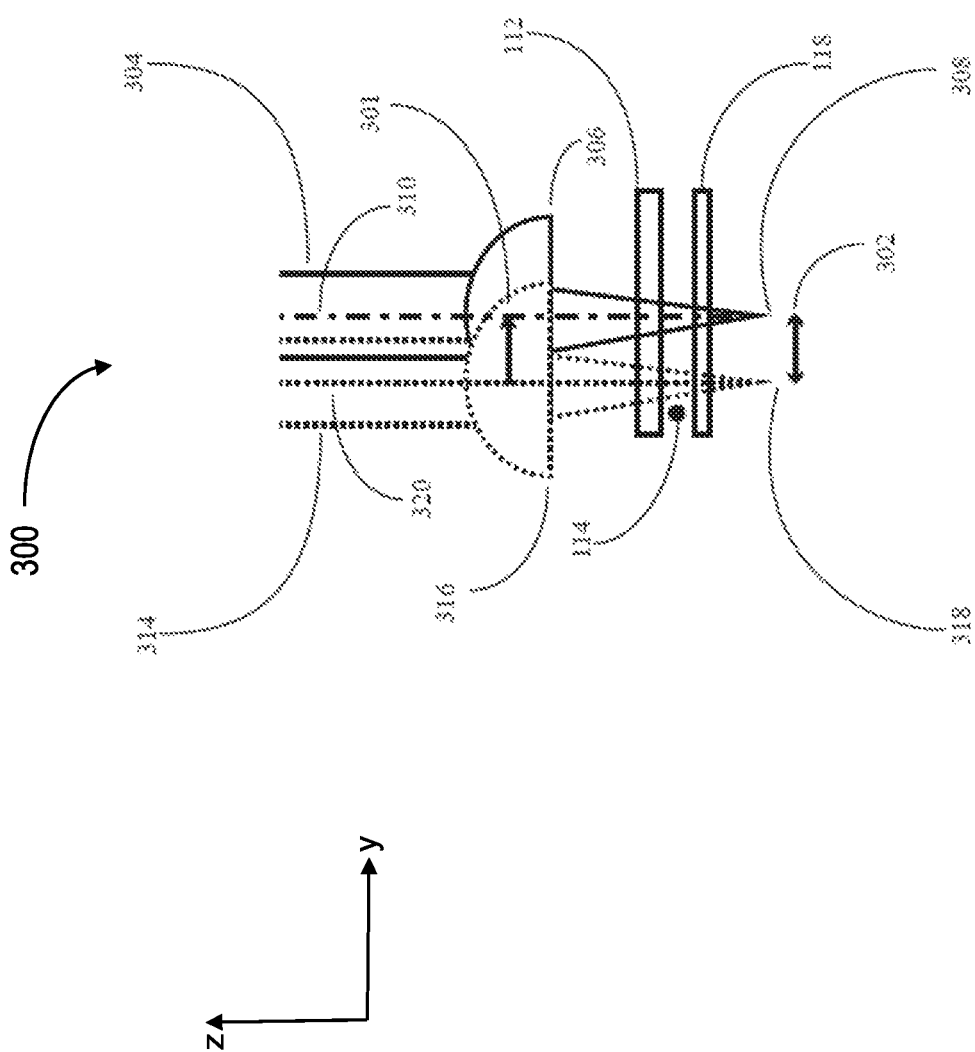
FIG. 3 schematically represents a system for scanning an electromagnetic radiation beam over at least one axes, according to some embodiments.

Referring now to FIG. 3, an embodiment of a system including a beam scanner 300 is schematically represented. A scan 301 of the optic/EMR beam can result in a translation (or rotation) of the focus location over a scan width 302. A scan width 302 is a distance over which the focus location changes laterally (i.e. x-axis and/or y-axis). In some implementations, the beam scanner 300 can scan (e.g., move) 301 the EMR focus, the optic and the optical axis (or EMR beam). FIG. 3 shows a scan 301 to a second EMR beam location 304, a second optic location 306, and a second focus location 308 (along optical axis 310) from a first EMR beam location 314, a first optic location 316, and a first focus location 318 (along optical axis 320). According to some implementations, the EMR beam and the optical axis remain incident on the first window 112, the chamber 114 and the second window 118 over the entire scan width. In some embodiments, the depth of the focus within a tissue can be controlled. For example, it can be desirable that a direction or plane of scan 301 be parallel with a distal surface 120 of the second window 118 to within a known specification. This is because, as described above, a change in a distance along the optical axis between the optic and the distal surface 120 of the second window can result in a change in the working distance 122, and the depth of the focus within the tissue. According to some embodiments, the second window 118 is held parallel to the scan motion within a specified angle (e.g., 10 mrad, 1 mrad, 0.5 mrad, or 0.1 mrad). Alternatively, in some implementations a change in working distance 122 over a scan width 302 can be limited to an acceptable range (e.g., 0.25 mm of working distance 122 change over a scan width of 10 mm). The beam scanner 300 can be controlled by a controller (e.g., controller 126). In some implementations, the controller can control one or more parameters of the beam scanner including: jump speed, acceleration, position, dwell time, etc.

Figure 4B:
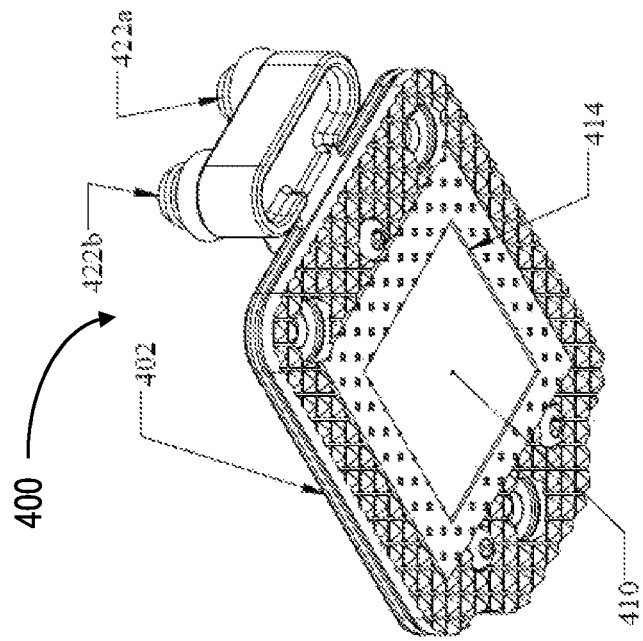
FIGS. 4A-4D schematically represents an embodiment of a system to cool a tissue coincident an irradiation in numerous views, according to some embodiments.
Figure 4A:
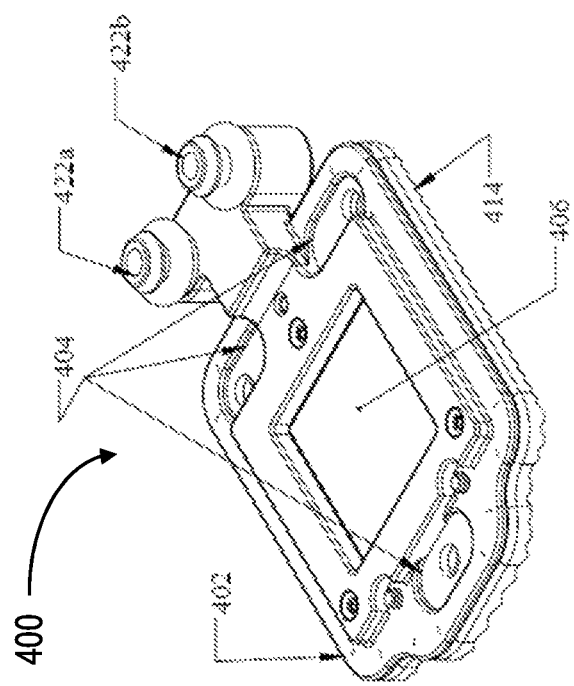
Figure 4C:
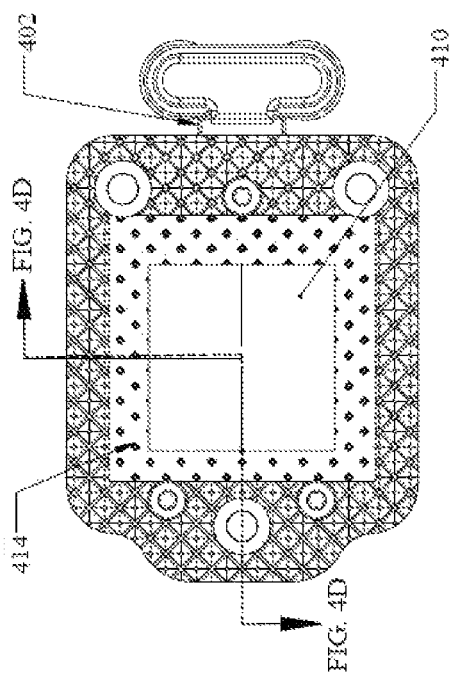
Figure 4D:
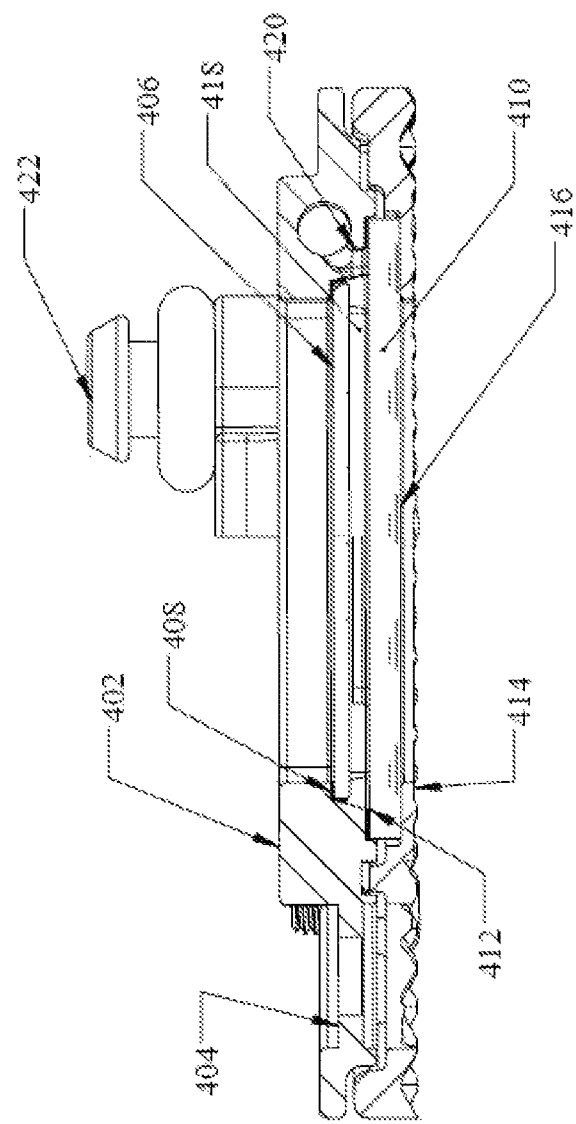

An exemplary cooling element 400 is schematically represented in various views in FIGS. 4A-4D. FIG. 4A illustrates a top isometric view of the cooling element 400 (e.g., portion of the cooling element 400 facing the EMR source/facing away from the target tissue). FIG. 4B shows a bottom isometric view of the cooling element 400 (e.g., portion of the cooling element 400 facing the target tissue/facing away from the EMR source). FIG. 4C shows a bottom view of the cooling element 400. FIG. 4D shows a section view of the cooling element 400, along the section lines shown in FIG. 4C. The exemplary cooling element 400 comprises a frame 402. Referring to FIGS. 4A and 4C, the frame 402 has three datums 404. The datums 404 correspond to a mount on an energy based device, which can generate an irradiation, thereby allowing the cooling element 400 to be removably attached and replaced on the energy based device. According to some embodiments, the datums 404 may approximate one or more geometric forms, for example a plane, a line, and a point. According to some versions, the datums 404 comprise a part of kinematic mount (e.g., Maxwellian mount). The three datums 404 of the exemplary cooling element 400 can be located in a plane. The exemplary cooling element 400 further includes a first window 406 sealed to the frame 402 by a first seal 408 and a second window 410 being sealed to the frame 402 by a second seal 412. According to some embodiments, the first seal 408 and the second seal 412 comprise an adhesive. Examples, of adhesives can include light cure adhesives, silicones, and epoxies. According to other embodiments, the first seal 408 and/or the second seal 412 include a weld, a braze, or a solder and the edges of the corresponding first window 406 and/or the second window 410 can be metallized, sputtered, or coated with a material (e.g., metal) allowing for this type of seal. Additionally, the second window 410 is affixed to the frame 402 with one or more fasteners 414. It can be seen in FIGS. 4C and 4D, the fastener 414 of the exemplary cooling element 400 includes a clamp plate held in place by 3 machine screws. Additional examples of a fastener can include a screw, a clamp, a snap a retaining ring, a tab, or any combination thereof. Affixing the second window 410 to the frame allows for the distal surface 416 of the second window 410 to be placed firmly in contact with tissue, without introducing additional stress to the second seal 412, which can result in flexure or movement of the distal surface of the second window.

As described above, a change in distance between the distal surface 416 and an optical element 106 focusing an EMR beam 104 affects the working distance 122 of the beam and a location of a resulting focus 108 within a tissue 101. According to some embodiments, the distal surface 416 of the second window 410 can be located at a predetermined geometry (e.g., orientation, location, etc.) relative the datum 404. For example in some versions, the second window 410 is located parallel to a plane approximated by one or more datums 404 to within a desired tolerance (e.g., 0.5 mrad). Additionally, the second window 410 can be located at a precise distance along the optical axis (e.g., z-axis) within a desired tolerance (e.g., 0.05 mm). Additionally, according to some embodiments, both the first window 406 and the second widow 410 are located parallel and a prescribed distance between them can be within desired tolerances (e.g., 0.5 mrad and 0.05 mm). In some implementations, the first window 406 and the second widow 410 can be arranged at an angle with respect to each other (e.g., at an angle less than 10 mrad). For various reasons, the distal surface 416 of the second window in some embodiments comprises a non-plano shape (e.g., convex or concave). For example, a convex shaped distal surface 416 can be advantageous for compressing a tissue when placed in contact with tissue.

FIG. 4D depicts a chamber 418 within the cooling element 400. The chamber 418 is bounded by the frame 402, the first window 406, and the second window 410. The chamber 418 can be sealed by the first seal 408 and the second seal 412. The chamber 418 is configured to contain a coolant. According to some embodiments, a flow of coolant is supplied to the chamber 418 through one or more ports 420 in fluidic communication with the chamber 418. According to some embodiments, the port 420 can provide for the flow of coolant from a coolant flow source, which is in fluidic communication with the port 420. In some implementations, the coolant flow source can be in fluidic communication with the port 420 by way of one or more fittings 422. FIGS. 4A and 4B illustrate both a coolant supply fitting 422a and a coolant return fitting 422b, for supplying coolant to and returning coolant from the chamber 418.

According to some embodiments, the second window comprises a material having a high thermal effusivity (e.g., quartz, sapphire, diamond, etc.). Higher thermal effusivity can allow for more heat to be transferred from the tissue surface to the flow of coolant. Likewise according to some embodiments, the first window 406 comprises a material having a lower thermal effusivity (e.g., a glass or a polymer). Implementations having a first window 406 with a lower thermal effusivity material can transfer less heat through the first window and into the flow of coolant. As a result, condensation can occur more slowly than in versions where the first window 406 comprises a high thermal effusivity material. Additionally, in some embodiments the first window has a thickness (e.g., 1 mm), which is greater than that of the second window (e.g., 0.5 mm), allowing thermal energy transfer to occur more freely across the second window. According to some versions, a non-condensing gas such as clean dry air, nitrogen, carbon dioxide, or argon can be blown against the first window to further prevent condensation.

Figure 5:
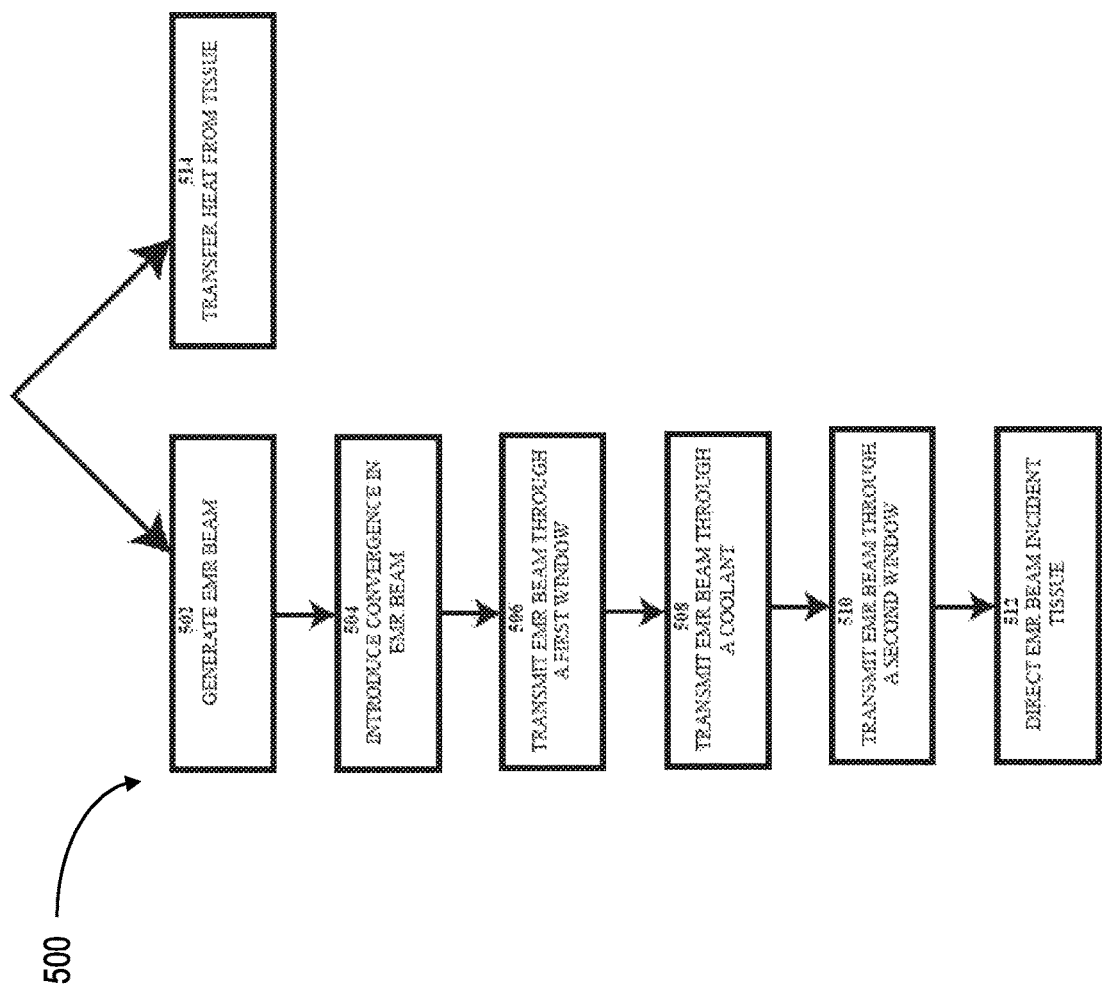
FIG. 5 is a flow chart representing a method for irradiating and cooling a tissue, according to some embodiments.

Referring now to FIG. 5, a flow chart is depicted that describes a method 500 for irradiating and cooling a tissue according to some embodiments. At 502, an electromagnetic radiation (EMR) beam is generated using an EMR source. At 504, a wave front change is introduced to the EMR beam that causes the EMR beam to converge as it propagates along an optical axis. At 506, the converging EMR beam is transmitted through a first window, a coolant adjacent the first window, and a second window 510 adjacent the coolant. Finally, the converging EMR beam is directed incident a surface area of a tissue 512. Concurrently, heat is transferred 514 from the surface area of the tissue to the coolant through the second window.

According to some embodiments of the method 500, the converging EMR beam ultimately comes to a focus within the tissue at a depth below the surface area of the tissue. In another version, the depth of the focus is varied over time. As described above, varying the depth of the focus within the tissue allows for treatments that require energy being delivered over a range of depths, for example in dermal melasma treatments. In some versions, the depth is varied over a range of between 0.001 mm to 10 mm. In some versions, the EMR beam at focus has an energy density sufficient to cause thermionic ionization in pigmented tissue (e.g., energy density greater than about 10 $J/cm^2$ for a 100 nanosecond pulse duration and 1064 nm wavelength).

According to some embodiments, the method 500 further comprises scanning the converging EMR beam over a scan width in one or more axes and causing the EMR beam to be directed 512 to a second surface area of the tissue. Typically, the EMR beam is a pulsed energy source and each pulse causes the EMR beam to be directed to a new surface area as it is scanned. In some versions, beam scanning is performed in one or more axes that are generally parallel to the distal surface of the second window (along x-y plane parallel to the second/first window), such that the depth of the focus varies no more than a desired tolerance over the scan width (e.g., 0.25 mm or 0.05 mm).

According to some embodiments, at 502, the EMR beam is generated at an average power at least as great as 1 W, 5 W, 10 W, or 30 W. According to some embodiments the EMR beam is generated at a wavelength in a range between 400 nm and 4000 nm. According to some embodiments the wave front change is introduced to the EMR beam 504 to result in a convergence of the EMR beam of a rate according to a numerical aperture (NA) of at least 0.3.

A table is provided below to summarize exemplary parameters and parameter ranges, according to some embodiments.

| PARAMETER | MIN. | NOM. | MAX. | UNITS |
|---|---|---|---|---|
| EMR Wavelength | 100 | 1064 | $15 \times 10^9$ | Nanometers |
| EMR Pulse Duration | $1 \times 10^{-5}$ | 100 | $10 \times 10^7$ | Nanoseconds |
| EMR Repetition Rate | 1 | $20 \times 10^3$ | $100 \times 10^3$ | Hertz |
| EMR Average Power | 0.1 | 30 | 100 | Watts |
| Numerical Aperture (NA) of Focus | 0.01 | 0.5 | 1.0 | N/A |
| Energy Density at Focus | <0.1 | 100 | >10,000 | $J/cm^2$ |
| Peak Power Density at Focus | <$10^9$ | $10^{11}$ | >$10^{13}$ | $W/cm^2$ |
| Working Distance of Focus | 0.001 | 0.3 | 100 | Millimeters |
| Coolant Temperature | −20 | 5 | 20 | ° C. |
| Coolant Flow Rate | 5 | 500 | 50000 | Milliliters per minute |
| Coolant Pressure | 0.1 | 10 | 150 | Pounds per square inch, gauge |
| Parallelism between Second Window and one or more Scan Axes | 100 | 0.1 | 0.001 | Milliradian |
| Thickness of Windows | 0.1 | 1 | 10 | Millimeters |
| Thickness of Coolant Chamber | 0.05 | 0.5 | 10 | Millimeters |
| Width of Windows | 1 | 10 | 100 | Millimeters |
| Scan Width of Scanned EMR Beam | 0.001 | 10 | 100 | Millimeters |
| Working Distance Tolerance over a Scan Width | 0.001 | 0.01 | 1 | Millimeters |
| Example Frame Material | Metals, such as stainless steel (e.g., 316L), aluminum, titanium, etc.; and polymers, such as Nylon, polycarbonate, Ultem, Radel, etc. | | | |
| Example Window Material | Transparent crystalline materials, such as quartz, sapphire, and diamond; and transparent amorphous materials, such as polymers and glass. | | | |
| Example Seal Materials | Adhesives, such as silicones, epoxies, etc.; and brazing, welding, and soldering materials, such as tin, nickel, etc. | | | |

Properties of Treatment Radiation

Figure 6:
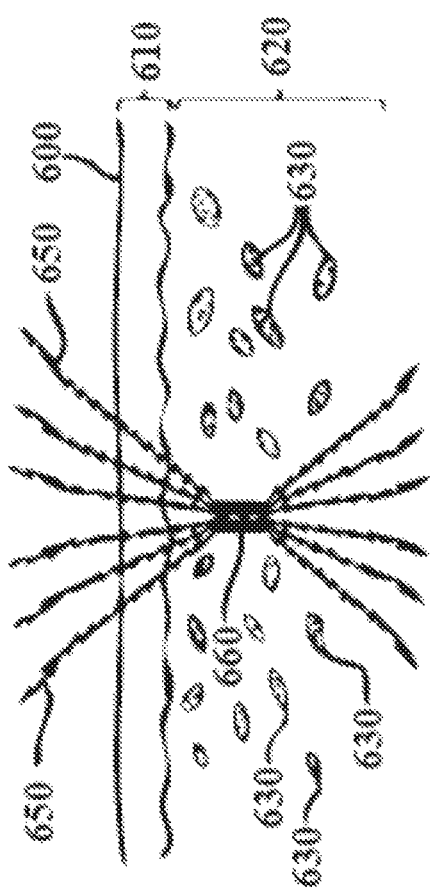
FIG. 6 is a schematic illustration of a laser beam focused into a pigmented region of a dermal layer in skin.

FIG. 6 is a schematic view of an illustration of a laser beam focused into a pigmented region of a dermal layer in a skin tissue. The skin tissue includes a skin surface 600 and an upper epidermal layer 610, or epidermis, which can be, e.g., about 30-120 μm thick in the facial region. The dermis can be slightly thicker in other parts of the body. For example, in general the thickness of the epidermis can range from about 30 μm (e.g., on the eyelids) to about 1500 μm (e.g., on the palm of the hand or soles of the feet). Such epidermis may be thinner or thicker than the examples above in certain conditions of the skin, for example psoriasis. The underlying dermal layer 620, or dermis, extends from below the epidermis 610 to the deeper subcutaneous fat layer (not shown). Skin exhibiting deep or dermal melasma can include a population of pigmented cells or regions 630 that contain excessive amounts of melanin. Electromagnetic radiation (EMR) 650 (e.g., a laser beam) can be focused into one or more focal regions 660 that can be located within the dermis 620, or the epidermis, 610. The EMR 650 can be provided at one or more appropriate wavelengths that can be absorbed by melanin. EMR wavelength(s) can be selected based on one or more criteria described below.

Figure 7A:
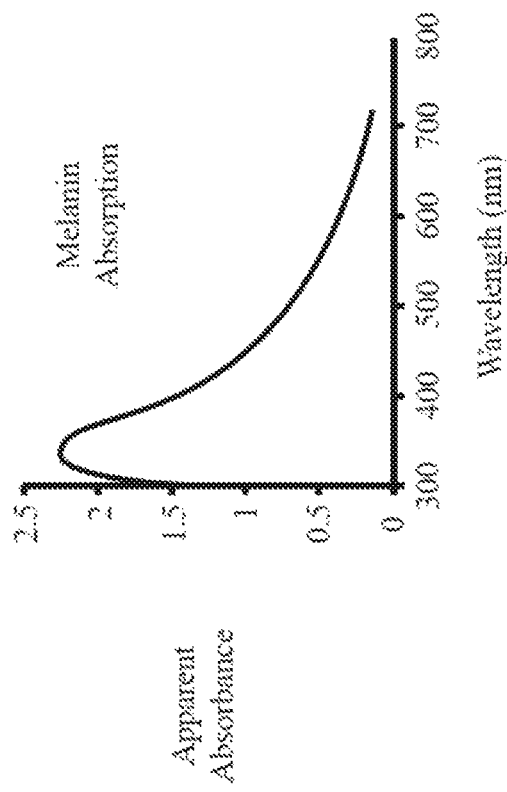
FIG. 7A is an exemplary absorbance spectrum graph for melanin.

Determination of desirable wavelength for treatment of certain skin conditions, such as pigmentary conditions and non-pigmentary conditions, can depend on, for example, the wavelength dependent absorption coefficient of the various competing chromophores (e.g., chromophore, hemoglobin, tattoo ink, etc.) present in the skin. FIG. 7A is an exemplary absorbance spectrum graph for melanin. The absorption of EMR by melanin is observed to reach a peak value at a wavelength of about 350 nm, and then decreases with increasing wavelength. Although absorption of the EMR by the melanin facilitates heating and/or disruption of the melanin-containing regions 630, a very high melanin absorbance can result in high absorption by pigment in the epidermis 610 and reduced penetration of the EMR into the dermis 620, or the epidermis 610. As illustrated in FIG. 7A, melanin absorption at EMR wavelengths that are less than about 500 nm are relatively high, such that wavelengths less than about 500 nm may not be suitable for penetrating sufficiently into the dermis 620 to heat and damage or disrupt pigmented regions 630 therein. Such enhanced absorption at smaller wavelengths can result in unwanted damage to the epidermis 610 and upper (superficial) portion of the dermis 620, with relatively little unabsorbed EMR passing through the tissue into the deeper portions of the dermis 620.

Figure 7B:
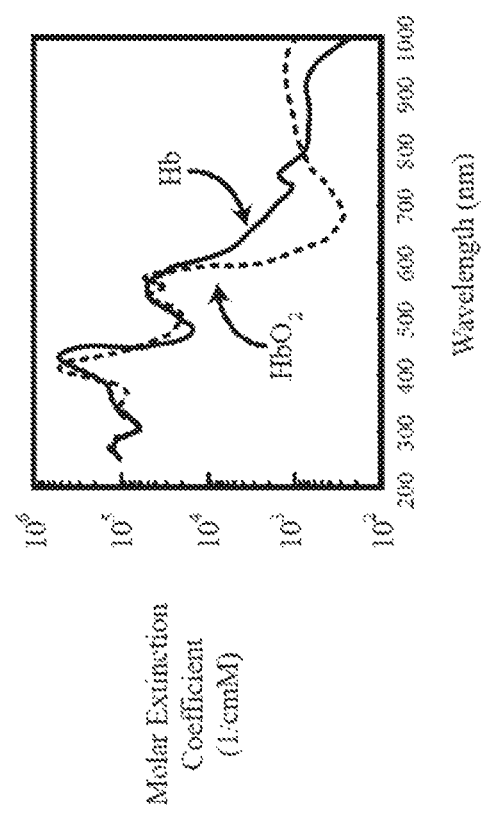
FIG. 7B is an exemplary absorbance spectrum graph for hemoglobin.

FIG. 7B is an exemplary absorbance spectrum graph for oxygenated or deoxygenated hemoglobin. Hemoglobin is present in blood vessels of skin tissue, and can be oxygenated ($HbO_2$) or deoxygenated (Hb). Each form of Hemoglobin may exhibit slightly different EMR absorption properties. As illustrated in FIG. 7B, exemplary absorption spectra for both Hb and $HbO_2$ indicate a high absorption coefficient for both Hb and $HbO_2$ at EMR wavelengths less than about 600 nm, with the absorbance decreasing significantly at higher wavelengths. Strong absorption of EMR directed into skin tissue by hemoglobin (Hb and/or $HbO_2$) can result in heating of the hemoglobin-containing blood vessels, resulting in unwanted damage to these vascular structures and less EMR available to be absorbed by the melanin.

Figure 8:
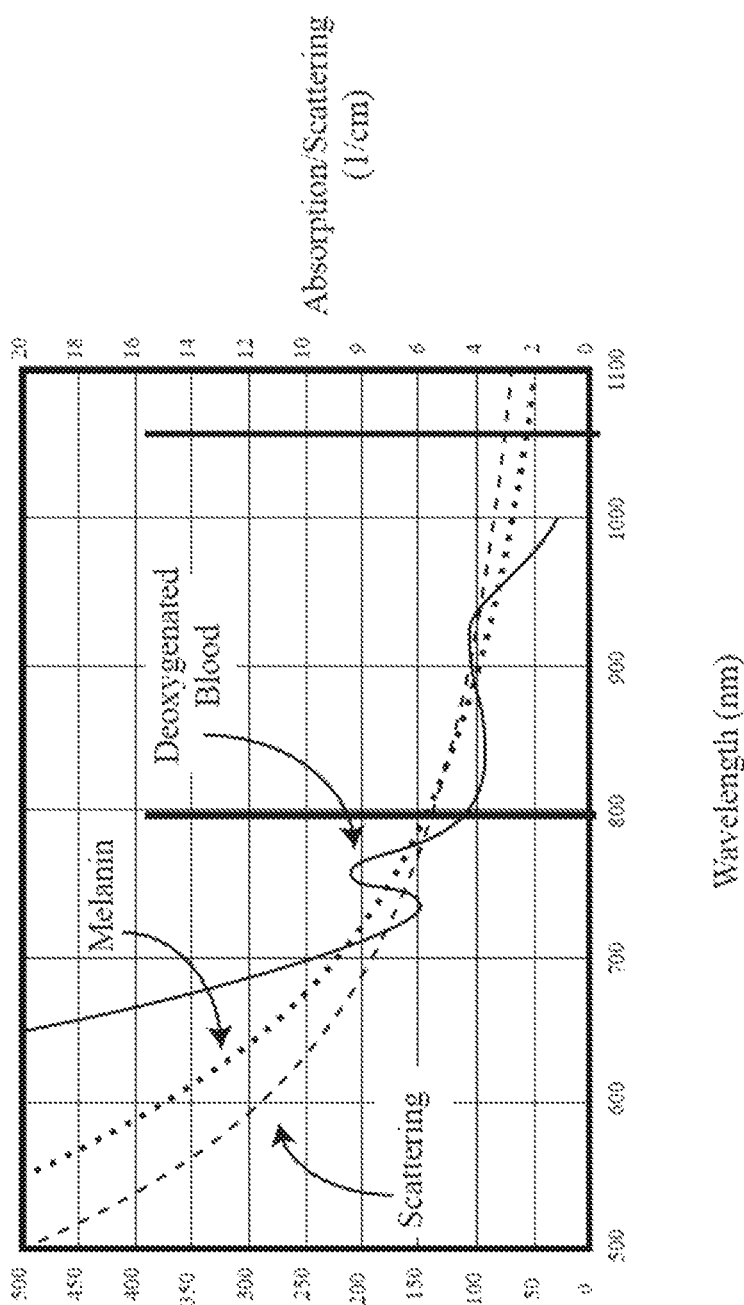
FIG. 8 illustrates a plot of the absorption coefficients of melanin and venous blood, and scattering coefficients of light in skin versus wavelength.

The choice of an appropriate wavelength for EMR can also depend on wavelength dependent scattering profile of tissues interacting with the EMR. FIG. 8 illustrates a plot of the absorption coefficient of melanin and venous blood versus wavelength. FIG. 8 also illustrates a plot of the scattering coefficient of light in skin versus wavelength. Absorption in melanin decreases monotonically with wavelength. If melanin is the target of a pigmentary condition treatment, a wavelength having a high absorption in melanin is desirable. This would suggest that the shorter the wavelength of light, the more efficient the treatment. However, absorption by blood increases at wavelengths shorter than 800 nm, thereby increasing the risk of unintentional targeting of blood vessels. In addition, as the intended target can be located below the skin surface, the role of scattering by skin (e.g., dermal layer) can be significant. Scattering reduces the amount of light that reaches the intended target. The scattering coefficient decreases monotonically with increasing wavelength. Therefore, while a shorter wavelength can favor absorption by melanin, a longer wavelength can favor deeper penetration due to reduced scattering. Similarly, longer wavelengths are better for sparing blood vessels due to a lower absorption by blood at longer wavelengths.

With the above considerations in mind, wavelengths can range from about 300 nm to about 3000 nm, and more particularly about 800 nm to about 1064 nm, can be used for selectively targeting certain structures (e.g., melanin) in the dermis. In particular, wavelengths of about 800 nm and about 1064 nm can be useful for such treatments. The 800 nm wavelength can be attractive because laser diodes at this wavelength are less costly and readily available. However, 1064 nm can be particularly useful for targeting deeper lesions due to lower scattering at this wavelength. A wavelength of 1064 nm can also be more suitable for darker skin types in whom there is a large amount of epidermal melanin. In such individuals the higher absorption of lower wavelength EMR (e.g., about 800 nm) by melanin in the epidermis increases the chances of thermal injury to the skin. Hence, 1064 nm may be a more suitable wavelength of the treatment radiation for certain treatments for some individuals.

Various laser sources can be used for the generation of EMR. For example, Neodymium (Nd) containing laser sources are readily available that provide 1064 nm EMR. These laser sources can operate in a pulsed mode with repetition rates in a range of about 1 Hz to 100 KHz. Q-Switched Nd lasers sources may provide laser pulses having a pulse duration of less than one nanosecond. Other Nd laser sources may provide pulses having pulse durations more than one millisecond. An exemplary laser source providing 1060 nm wavelength EMR is a 20 W NuQ fiber laser from Nufern of East Granby, Conn., USA. The 20 W NuQ fiber laser provides pulses having a pulse duration of about 100 ns at a repetition rate in the range between about 20 KHz and about 100 KHz. Another laser source, is an Nd:YAG Q-smart 850 from Quantel of Les Ulis, France. The Q-smart 850 provides pulses having a pulse energy up to about 850 mJ and a pulse duration of about 6 ns at a repetition rate of up to about 10 Hz.

The systems described herein can be configured to focus the EMR in a highly convergent beam. For example, the system can include a focusing or converging lens arrangement having a numerical aperture (NA) selected from about 0.3 to 0.9 (e.g., between about 0.4 and 0.9). The correspondingly large convergence angle of the EMR can provide a high fluence and intensity in the focal region of the lens (which can be located within the dermis) with a lower fluence in the overlying tissue above the focal region. Such focal geometry can help reduce unwanted heating and thermal damage in the overlying tissue above the pigmented dermal regions. The exemplary optical arrangement can further include a collimating lens arrangement configured to direct EMR from the emitting arrangement onto the focusing lens arrangement.

The exemplary optical treatment systems can be configured to focus the EMR to a focal region having a width or spot size that is less than about 200 µm, for example, less than about 100 µm, or even less than about 50 µm, e.g., as small as about 1 µm. For example, the spot size can have ranges from about 1 µm to about 50 µm, from about 50 µm to about 100 µm, and from about 100 µm to about 200 µm. The spot size of the focal region can be determined, for example, in air. Such spot size can be selected as a balance between being small enough to provide a high fluence or intensity of EMR in the focal region (to effectively irradiate pigmented structures in the dermis), and being large enough to facilitate irradiation of large regions/volumes of the skin tissue in a reasonable treatment time.

The exemplary optical arrangement can also be configured to direct the focal region of the EMR onto a location within the dermal tissue that is at a depth below the skin surface, such as in the range from about 30 µm to about 2000 µm, e.g., between about 150 µm to about 500 µm. Such exemplary depth ranges can correspond to typical observed depths of pigmented regions in skin that exhibits dermal melasma or other targets of interest. This focal depth can correspond to a distance from a lower surface of the apparatus configured to contact the skin surface and the location of the focal region. Additionally, some embodiments can be configured for treating targets within the epidermis. For example, an optical arrangement may be configured to direct a focal region of the EMR to a location within the epidermis tissue, for example in a range from about 5 µm to 2000 µm beneath the skin surface. Still other embodiments may be configured for treating a target deep in the dermis. For example, a tattoo artist typically calibrates his tattoo gun to penetrate the skin to a depth from about 1 mm to about 2 mm beneath the skin surface. Accordingly, in some embodiments an optical arrangement may be configured to direct a focal region of the EMR to a location within the dermis tissue in a range from about 0.4 mm to 2 mm beneath the skin surface.

EXAMPLE

Figure 9A:
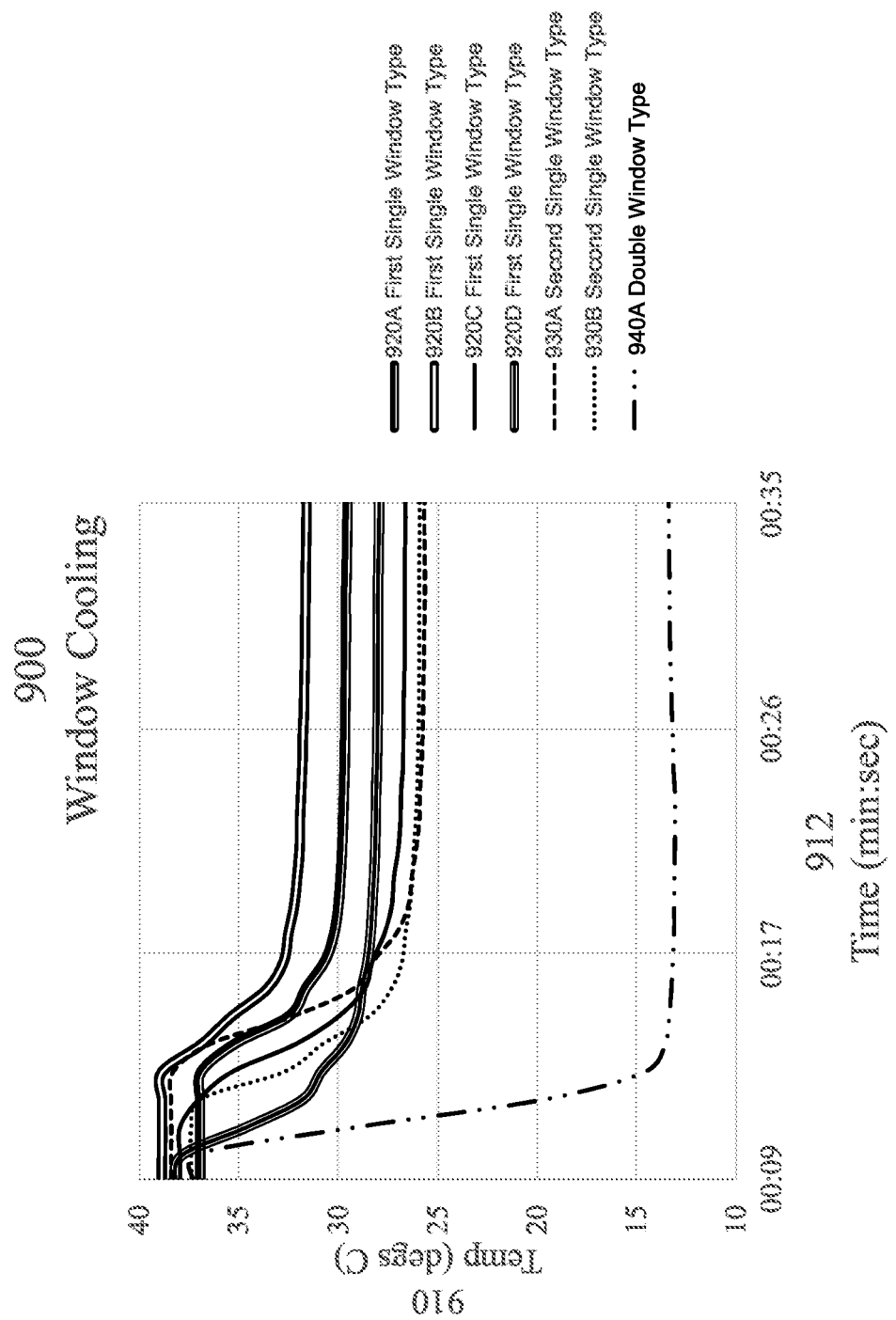
FIG. 9A illustrates a graph depicting cooling performance of multiple exemplary cooling elements.
Figure 9B:
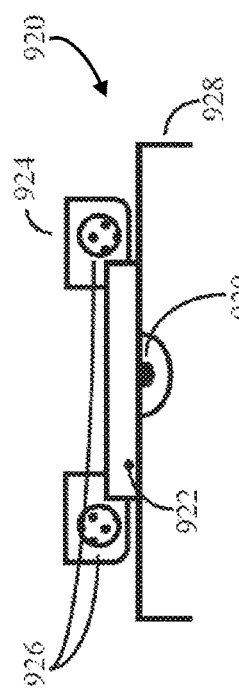
FIGS. 9B-9D illustrate schematics of exemplary cooling elements.
Figure 9C:
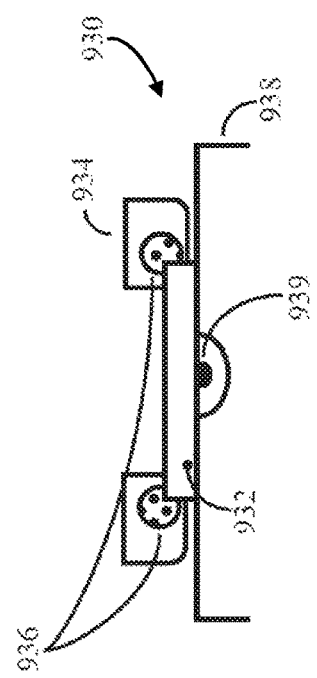
Figure 9D:
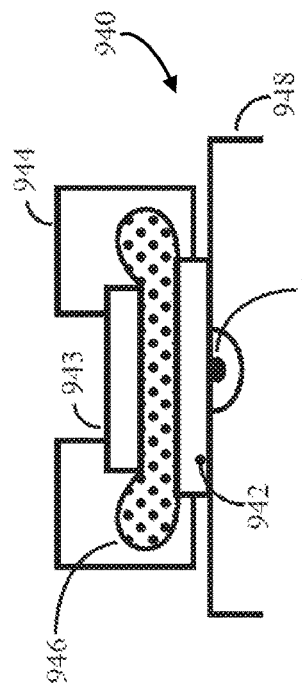

FIG. 9A illustrates multiple plots depicting cooling performance of multiple exemplary cooling elements (e.g., cooling elements in FIGS. 9B-9D). Data shown in FIG. 9A was collected during an experiment conducted with cooling elements 920, 930 and 940. The graph 900 has temperature displayed in degrees Celsius along a vertical axis 910 and time (in minutes and seconds) displayed along a horizontal axis 912.

Each cooling element was placed in a test fixture block, and a thermocouple was placed in the middle of a first surface of the cooling element. Thermal paste was used to ensure thermal conduction between the first surface of the cooling element and the thermocouple. The cooling element was placed with the first surface in contact with a dry bath. The dry bath was set to 37° C. and each cooling element was allowed to approach thermal equilibrium with the dry bath. Finally, a chilled fluid at 5° C. was provided to the cooling element, and the thermocouple captured temperature measurements of the first surface of the window as it cooled.

FIGS. 9B-9D illustrate schematics of exemplary cooling elements that were tested as part of the experiment discussed above. Exemplary embodiment of the cooling element are a first single window type cooling element 920, a second single window type cooling element 930, and a double window type cooling element 940. FIG. 9B illustrates the single window type cooling element 920 that includes a single sapphire window 922 in contact (e.g., along the edges of the sapphire window) with an aluminum heat exchanger 924 inside which the coolant 926 flows. Heat flows from the dry bath 928 to the middle of the first surface of the sapphire window 922 (e.g., surface adjacent to the dry bath 928), horizontally through the sapphire window 922 to the edges of the sapphire window 922, through the aluminum heat exchanger 924 and into the coolant 926. Temperature of the first surface of the window 922 is measured by a thermocouple 929.

FIG. 9C illustrates the single window type cooling element 930 comprising a single sapphire window 932 which is sealed to a manifold 934 inside which the coolant 936 flows. Single window type cooling element 930 is configured to allow the coolant 936 to come in direct contact with the single sapphire window 932 around the edges of the window 932. Heat flows from the dry bath 938 to the center of the first surface of the window 932 (e.g., surface adjacent to the dry bath 938), the edges of window 932 and directly into the coolant 936. Temperature of the first surface of the window 932 is measured by a thermocouple 939.

FIG. 9D illustrates the double window type cooling element 940 comprising a first window 942, a second window 943, a frame 944, and a coolant 946 flowing between the first and second windows. Heat flows from the dry bath 948 to the center of the first surface of the first window 942 (e.g., surface adjacent to the dry bath 948), vertically through the first window 942, and into the coolant 946. Temperature of the first surface of the first window 942 is measured by a thermocouple 949.

Returning to FIG. 9A, cooling data for cooling elements 920, 930 and 940 are shown. The first set of plots 920A-D represent cooling data for the first single window type cooling element 920, the second set of plots 930A-B represent cooling data for the second single window type cooling element 930, and the third plot 940A represents cooling data for the double window type cooling element 940. The plots indicate improvement in cooling for the second single window type cooling element 930 over the first single window type assembly 920. However, the double window type cooling element 940 shows great improvement over both first and second single window type assemblies. The double window type cooling element 940 data shows cooling approaching a steady state temperature of about 13.4° C. A lowest measured window surface temperature for the second single window type cooling element 930, which approaches a steady state temperature of about 25.9° C. The double window type cooling element 940 can cool to a temperature 12.5° C. which can be cooler than the best performing single window type assembly. The graph 900 also shows that cooling occurs faster with the double window type cooling element 940. A thermal time constant (e.g., time for window to cool about 63.2% of an initial temperature) for the first and single window type assemblies is estimated at about 4 seconds based on the data. And, a thermal time constant for the double window type assembly is estimated at about 2 seconds or half that of the single window type assemblies.

Methods of treating various skin conditions, such as for cosmetic purposes, can be carried out using the systems described herein. It is understood that although such methods can be conducted by a physician, non-physicians, such as aestheticians and other suitably trained personnel may use the systems described herein to treat various skin conditions with and without the supervision of a physician.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

The invention claimed is:

1. A system comprising:
   an optical element configured to receive an electromagnetic radiation (EMR), and focus the EMR along an optical axis to a focal region in a target tissue;
   a controller configured to direct the optical element along a first scan path, wherein a motion of the optical element along the first scan path is configured to traverse the focal region along a treatment path in the target tissue;
   a cooling element down-beam from the optical element and configured to be removably attached to the system via three or more datums and to receive the focusing EMR, the cooling element comprising:
      a first window comprising a first proximal surface and a first distal surface;
      a second window down-beam from the first window, the second window comprising a second proximal surface and a second distal surface, wherein the second window is configured to contact the target tissue or a tissue adjacent to the target tissue via the second distal surface, and wherein the first scan path is parallel to the second distal surface within 50 milliradians;
      a coolant chamber located between the first distal surface of the first window and the second proximal surface of the second window and configured to receive a coolant.

2. The system of claim 1, wherein the controller is configured to vary a first distance between the focal region and the second distal surface of the second window along the optical axis by varying a second distance between the optical element and the second distal surface of the second window along the optical axis.

3. The system of claim 2, wherein the first distance varies between a first predetermined value and a second predetermined value as the focal region traverses along the treatment path in the target tissue.

4. The system of claim 3, wherein a difference between the first predetermined value and the second predetermined value is less than 0.25 mm.

5. The system of claim 3, wherein the first predetermined value is 0.001 mm and the second predetermined value is 10 mm.

6. The system of claim 1, wherein the controller is configured to vary a first distance between the focal region and the second distal surface of the second window along the optical axis by varying a divergence associated with the EMR.

7. The system of claim 1, further comprising a scanner, wherein the scanner is configured to receive a control signal from the controller and move the optical element along the first scan path perpendicular to the optical axis based on the control signal.

8. The system of claim 1, wherein the first scan path is substantially parallel to the second distal surface of the second window.

9. The system of claim 1, wherein the controller is configured to vary an intensity of the EMR.

10. The system of claim 1, wherein the controller is configured to vary a flow rate of the coolant in the coolant chamber.

11. The system of claim 1, wherein the optical element has a numerical aperture (NA) in the range of about 0.1 to about 1.0.

12. The system of claim 1, wherein the EMR has an average power in the range of about 1 W to about 100 W.

13. The system of claim 1, wherein the EMR includes a pulsed laser beam having a wavelength in a range of about 400 nm to about 4000 nm.

14. The system of claim 1, wherein the EMR is configured to generate thermionic plasma in the focal region.

15. The cooling element of claim 1, further comprising a gas source configured to direct a gas at the first window, the gas configured to prevent condensation on the first window.

16. The system of claim 1, wherein the first window has a first thermal effusivity and the second window has a second thermal effusivity that is greater than the first thermal effusivity.

17. The system of claim 1, wherein the first window and the second window are sealed to a frame of the cooling element via a first seal and a second seal, respectively, wherein the first and the second seals include one or more of a weld, a braze and a solder.

18. The system of claim 1, wherein the optical element is configured to change a location of the focal region along the optical axis by traveling along the optical axis.

19. The system of claim 1, wherein the treatment path and the second distal surface are parallel within 50 milliradians.

20. A method comprising:
generating, by an optical element, a focusing electromagnetic radiation (EMR) configured to focus to a focal region in a target tissue;
transmitting the focusing EMR through a cooling element configured to be removably attached to the system via three or more datums, wherein the cooling element includes:
  a first window comprising a first proximal surface and a first distal surface,
  a second window down-beam from the first window, the second window comprising a second proximal surface and a second distal surface, wherein the second window is configured to contact a target tissue or a tissue adjacent to the target tissue via the second distal surface, and
  a coolant chamber located between the first distal surface of the first window and the second proximal surface of the second window and configured to receive a coolant; and
directing the optical element along a first scan path, wherein a motion of the optical element along the first scan path is configured to traverse the focal region along a treatment path in the target tissue, wherein the first scan path is parallel to the second distal surface within 50 milliradians.

21. The method of claim 20, wherein generating the focusing EMR comprises includes placing the optical element along an optical axis of the EMR.

22. The method of claim 21, further comprising varying a depth of the focal region in the target tissue by varying a location of the optical element along the optical axis.

23. The method of claim 22, wherein the depth of the focal region ranges from about 0.001 mm to about 10 mm.

24. The method of claim 20, further comprising scanning the focusing EMR along the treatment path in the target tissue.

25. The method of claim 24, wherein the focusing EMR beam is scanned along a treatment path by moving the optical element substantially parallel to the second distal surface of the second window.

26. The method of claim 25, wherein the treatment path is substantially parallel to the second distal surface of the second window.

27. The method of claim 20, wherein the first window has a first thermal effusivity and the second window has a second thermal effusivity that is greater than the first thermal effusivity.

28. The method of claim 20, further comprising moving the optical element along the optical axis, wherein moving the optical element is configured to change a location of the focal region along the optical axis.

29. The method of claim 20, further comprising directing a non-condensing gas at the first proximal surface.

* * * * *